(12) United States Patent  (10) Patent No.: US 8,657,796 B2
Marasco  (45) Date of Patent: Feb. 25, 2014

(54) WOUND IRRIGATION CONTAINMENT ARRANGEMENT

(76) Inventor: Patrick V. Marasco, Boxford, MA (US)

( * ) Notice: Subject to any disclaimer, the term of this patent is extended or adjusted under 35 U.S.C. 154(b) by 719 days.

(21) Appl. No.: 12/924,127

(22) Filed: Sep. 21, 2010

(65) Prior Publication Data

US 2011/0015560 A1   Jan. 20, 2011

Related U.S. Application Data

(60) Division of application No. 12/806,290, filed on Aug. 9, 2010, now Pat. No. 8,568,375, which is a continuation-in-part of application No. 11/232,456, filed on Oct. 19, 2005, now Pat. No. 7,771,402, which is a continuation-in-part of application No. 10/684,960, filed on Oct. 14, 2003, now abandoned, which is a continuation-in-part of application No. 09/621,636, filed on Jul. 21, 2000, now Pat. No. 6,635,035, which is a continuation-in-part of application No. 09/561,978, filed on May 2, 2000, now Pat. No. 6,562,013, which is a continuation-in-part of application No. 09/156,115, filed on Sep. 18, 1998, now Pat. No. 6,083,209, which is a continuation-in-part of application No. 08/682,888, filed on Jul. 11, 1996, now Pat. No. 5,848,998.

(51) Int. Cl.
*A61M 35/00* (2006.01)

(52) U.S. Cl.
USPC .................. 604/289; 128/202.12; 128/205.26

(58) Field of Classification Search
USPC ................ 604/289, 290; 128/202.12, 205.26
See application file for complete search history.

(56) References Cited

U.S. PATENT DOCUMENTS

| 4,996,992 A * | 3/1991 | LaViola et al. ................ 600/490 |
| 2009/0126727 A1 * | 5/2009 | Loori et al. ............... 128/202.12 |

* cited by examiner

*Primary Examiner* — Melanie Hand
(74) *Attorney, Agent, or Firm* — Don Halgren

(57) ABSTRACT

A containment arrangement for safely and effectively treating a wound on a patient without contaminating attending personnel. The arrangement comprises a patient receiving first enclosure having a patient contacting periphery, a pressurizable source in communication with the patient through a wall of the enclosure for enlarging the enclosure, and a sealing means arranged in the patient contacting periphery. A hand manipulable fluid discharge nozzle is extendably arranged through the enclosure for providing controllable treatment fluid to the wound on the patient within the enclosure.

20 Claims, 4 Drawing Sheets

WOUND IRRIGATION CONTAINMENT ARRANGEMENT

This application is a division of Ser. No. 12/806,290, filed 9 Aug. 2010, now U.S.Pat.No.8,568,375 which is a continuation-in-part application of Ser. No. 11/232,456, filed 19 Oct. 2005, now U.S. Pat. No. 7,771,402, which is a continuation-in-part application of patent application Ser. No. 10/684,960, filed 14 Oct. 2003, now abandoned which is a continuation-in-part application of patent application Ser. No. 09/621,636 filed Jul. 21, 2000 now U.S. Pat. No. 6,635,035, which is a continuation-in-part application of Ser. No. 09/561,978, filed May 2, 2000 now U.S. Pat. No. 6,562,013 which is a continuation-in-part application of Ser. No. 09/156,115, filed Sep. 18, 1998 now U.S. Pat. No. 6,083,209, which is a continuation-in-part of application Ser. No. 08/682,888, filed Jul. 11, 1996 now U.S. Pat. No. 5,848,998 each of which are incorporated herein by reference.

BACKGROUND OF THE INVENTION

1. Field of the Invention

This invention relates to the enclosure system for treating of wounds on body parts which system includes disposable collection bags therewith.

2. Prior Art

Wound treatment and containment is a concept who's time has come. The increase in contamination and possible medical personnel injury is serious due to the increased size of the population having contagious diseases. The treatment process must include means for safe disposal of any patient tissue and any treatment material or treatment fluids.

It is an object of the present invention to overcome the disadvantages of the prior art.

It is a further object of the present invention to provide a wound or patient irrigation containment arrangement which maximizes the treatment capabilities of the medical personnel, and maximizes the safety considerations for those medical personnel.

It is yet a still further object of the present invention to provide a wound treatment system for providing a containment arrangement which is less irritating to the patient, which treatment system may be stabilized and maintained about the patient for an extended period of time.

It is yet a further object of the present invention to provide a wound containment system which is portable to permit such use to be performed in the field, in a home or any environment where such a need occurs.

BRIEF SUMMARY OF THE INVENTION

The present invention comprises a wound containment arrangement for enclosing a wound on the surface of a patient. The wound enclosure arrangement, for example, may comprise an elongated flexible generally tubular plastic bag having a closed distal end and an open proximal end.

The open proximal end in a first embodiment thereof, has a skin engaging cuff arranged therearound. The elongated enclosure bag itself, has one or more entry ports disposed thereon external thereto. Each respective entry port has an internally directed duck bill valve arranged thereadjacent. The entry port and the duck bill valve thus are in longitudinal alignment and are in fluid communication with one another. The entry port and duck bill valve permits a nozzle of a gun type control to extend therethrough.

A gun type control mechanism permits the aiming and fluid control of a pressurized liquid or gas jetted therethrough from the nozzle onto the wound site for treatment within the enclosure bag. The enclosure bag in one preferred embodiment has at least one duck bill drain valve arranged on a lower portion thereof which duck bill valve is in fluid communication with a drain line which leads to a collection bag. The drain line and collection bag have a duck bill valve entry to permit the bag to receive but not leak any collection of debris from the patient being treated.

A sanitizer means is preferably disposed in a dissolvable pouch which pouch is disposed within the collection bag. The sanitizer permits the dis-infection and decontamination of any fluid or debris collected from the wound of the patient being treated in the enclosure bag.

The cuff at the proximal end of the enclosure bag in one embodiment, may have a soft, tissue sensitive, foraminous annular surface with a fluid conduit extending therearound. That fluid conduit in the cuff is in fluid communication with a suction pump arranged downstream thereof. The suction system permits a vacuum to be applied to the cuff so as to snugly and safely secure the proximal open end of the enclosure bag to the skin of the patient, while may also extract any extra contaminants or wound debris, but not irritably rubbing against a limb or surface of the patient being treated.

In yet a further object of the present invention, an air vent with a pressurizable, temperature regulatable air, liquid or gaseous treatment fluid supply may be arranged in fluid communication through the enclosure bag. The air vent may be in communication with a pump to provide the air, liquid or treatment gases within the enclosure bag so as to space the enclosure bag a distance apart from the skin of the patient therewithin. The enclosure bag may have an air pressure relief valve, to control or limit fluid pressure and permit the pressurized air provided to the enclosure bag to gently escape, thus maintaining a constant or controllable pressure and/or temperature and/or medicament supply within the bag and against the patient's skin.

A further embodiment of the present invention is contemplated by a flexible bubble-like enclosure arrangement which may be of generally hemispherical shape with an annular edge or lip extending therearound for attachment to the patient's skin. The bubble could also be of elongated or annular shape in other embodiments. The bubble is designed to be placed over a wound site of the patient. Such an enclosure bubble may have one or more input ports on an outer or external side of the pressurized enclosure bubble, and a corresponding duck bill inlet valve arranged in longitudinal alignment with the input port(s) on the inside surface of that enclosure bubble. The input port and the duck bill valve are in longitudinal alignment so as to permit the barrel of a pressurizable fluid supply nozzle to extend therethrough. The barrel and nozzle would be part of a gun type control mechanism which permits the aiming and the pressure, temperature or fluid mix control of a pressurized wound cleansing or medicament fluid(s) passing therethrough. The inlet valve, through which the elongated barrel and nozzle extends, itself may be elongated so as to sterilely enclose that elongated portion of the barrel, to eliminate the need for subsequent sterilization of that barrel in a further use thereof. The distal tip of the nozzle may be of stepped diameter so as to snuggly mate through an innermost opening of the inlet valve, thereby making only the nozzle sterilizable or replaceable during subsequent use thereof. The nozzle tip may be unscrewably removable from the barrel to facilitate that replacement or cleansing.

The enclosure bubble in this embodiment may also include an arrangement of wires extending around the annular lip of the enclosure bubble, the wires connected to a controllable electrical source to provide electrical or rf stimulation in an encompassing annular or rectilinear pattern around the wound of the patient, so as to promote healing and stimulate healing and normal tissue growth. A drainage conduit may extend under or through the side of the wall of the enclosure bubble and into a collection bag as identified hereinabove. An air seepage vent may be arranged adjacent the input and duck bill valve arrangement or a spot nearby. Such seepage port will provide a controlled pressure and temperature atmosphere within the enclosure bubble arrangement on the patient. A conduit may be in communication with a controllable suction pump, in which the conduit is in fluid communication with a section cuff disposed in the annular lip or peripheral lip of the enclosure bubble. Such a suction would help hold the enclosure bubble to the patient with minimum adverse reaction to the patient, and also provide a secondary drain for treatment fluid removal. Further patient skin attachment systems may of course include adhesive or bandages of the like.

In yet a further embodiment of the present invention comprises a plurality of enclosure bags successively disposed onto or about a patient's limb. In an operative example, such an inner and outer bag would be elongated so as to, for example fit over a patient's leg or foot having an opened end at its proximal end thereof. Such opened end would be fitted against a patient's leg and held thereagainst by a suction cuff as in the aforementioned embodiment. In the yet further embodiment of the present invention, it is contemplated that a plurality of wire loops may be arranged peripherally about the inner side or the outer bag, on the outer side of the inner bag, or disposed between the spaced apart enclosure bags. The loops pattern of wire are in electrical communication with a controllable electrical source so as to provide either heating, radio frequency (rf) treatment or those wires could be piezoelectric arrangement to generate wave induced energy for ultrasound treatment of the wound therewithin.

It is still contemplated that an inner end of an inner duck bill valve would be in fluid communication with an outer port arranged in the outer bag. The nozzle of a treatment gun would extend through the outer port and the inner duck bill valve so as to permit controlled treatment fluid to be pressurizably disposed against the wound within the inner enclosure bag. Such a further embodiment would include a duck bill valve extending through a conduit which is in communication with the innermost enclosure bag. The duck bill valve would be in fluid communication with a conduit which extends to a collection bag. A duck bill valve would be arranged within the collection bag so as to prevent any backflow of contaminated fluid extending to return into the inner enclosure bag.

It is further contemplated that a pressure source might direct fluid either gaseous matter or hardenable liquid between the inner bag and the outer enclosure bag. An air/fluid seepage patch might be arranged on the outer surface of the outer bag to permit controlled release and separation between the inner bag and the outer bag. A higher pressure fluid discharge nozzle may be arranged through both the outer and the inner bags so as to provide the fluid pressure to the patient's tissue within the inner bag. Such a high pressure source would controllably separate the inner bag from the patient's skin.

The fluid source arranged in communication with the outer bag from the pressure source through the outer bag may be replaced by an injection component for splinting the patient's limb/leg which is enclosed within the inner bag. Such a form could press the inner bag against the patient's limb and be contained within the confines of the outer bag to provide a splint for a broken limb or the like.

It is further contemplated by the present invention, that portions of the inner and/or the outer bag may be an electrically conductive plastic and/or thermally conductive or reflective or piezo stimulative for treating or heating tissue at the patient's wound site within the inner enclosure.

Thus it has been shown a unique combination of treatment and containment for a wound which treatment and containment may be done by trained medical personnel and/or by emergency workers. Such containment system provides a sterile atmosphere and an arrangement for keeping the patient from becoming contaminated himself.

The invention thus comprises a containment arrangement for safely and effectively treating a wound on a patient without contaminating attending personnel, comprising a patient receiving first enclosure having a patient contacting periphery, a pressurizable source in communication with the patient through a wall of the enclosure for enlarging the enclosure. A sealing means is arranged in the patient contacting periphery. A hand manipulable fluid discharge nozzle is extendably arranged through the enclosure for providing controllable treatment fluid to the wound on the patient within the enclosure. The sealing means may comprise a suction arrangement to hold the periphery of the first enclosure against the patient. The sealing means may also comprise a contaminated fluid removal system. The nozzle may extend through an inlet port and a one way valve. The containment system may include an electric treatment means arranged in the first enclosure. The treatment means may comprise an arrangement of electrically conductive members arranged around the first enclosure. The first enclosure has a peripheral lip, and wherein the conductive members are arranged in the lip of the first enclosure. The conductive members may be arranged on a wall portion of the first enclosure. The containment system may include a second enclosure arranged outwardly of the first enclosure. A separate pressurizable system may be arranged for the second enclosure. The separate pressurizable system for said second enclosure may include a fluid injecting arrangement and a pressure releasing arrangement. The separate pressurizable system for said second enclosure may also comprise a foam injection arrangement to provide a splint forming arrangement for the patient. The enclosure may comprise a metalized plastic to permit radio frequency treatment of the wound of the patient within the enclosure. An arrangement of conduction controlled electrical conduits may be arranged within the outer enclosure about the patient. The enclosure preferably has a contaminated fluid collection bag attached thereto, by a conduit therebetween, the collection bag containing a fluid sanitizer means therein.

The inventive containment and treatment system also includes a cuff arranged therewith for sensing a patient's medical condition. The cuff preferably includes a tourniquet for preventing blood loss from the patient using the system. The containment system may include a patient monitoring and reporting arrangement therewith for monitoring and reporting vital signs of the patient being treated therewith. The monitoring and reporting arrangement may include a radio signal beacon generation arrangement for reporting the physical location of the patient being treated. The inlet port may comprise a sealed or fluid tight arrangement around a distal end of the barrel and nozzle arrangement. The nozzle is preferably removable from said barrel.

The invention thus also comprises a containment arrangement for safely and effectively treating a wound on a patient without contaminating attending personnel, comprising: a patient-receiving first enclosure having a patient contacting periphery; a patient-sealing arrangement on the patient contacting periphery of the enclosure; a hand manipulable patient-treating fluid discharge gun extendable through the enclosure for providing controllable treatment fluid to the wound on the patient within the enclosure. The patient-sealing arrangement may comprise a suction arrangement to hold the periphery of the first enclosure against the patient. The patient-sealing arrangement may comprise an adhesive for securing the enclosure to the patient. The patient-sealing arrangement may comprise a contaminated-fluid removal system. The nozzle may extend through an inlet port and a one way valve. The fluid discharge gun may comprise a barrel and a distal nozzle thereon. The nozzle may be removable from the barrel to permit re-use of the discharge gun and its barrel, with a new uncontaminated nozzle on a new patient. The containment system may include a drainage conduit and a waste treatment fluid collection container for removing the treatment fluid from the enclosure. The drainage conduit may be gravity fed. The drainage conduit may be fed waste treatment fluid by a pressure from within the enclosure. The enclosure may be held at atmospheric pressure during the treatment of a patient therein. The enclosure may be held at above atmospheric pressure during the treatment of a patient therein. The enclosure may be held at below atmospheric pressure during the treatment of a patient therein. The enclosure may be held at a variable pressure during the treatment of a patient therein. The first enclosure may have a second patient-treating enclosure spaced therearound.

The invention also includes a pulsatile lavage arrangement for the prevention of aerosol contamination so as to safely and effectively treat a wound on a patient without contaminating attending personnel and associated equipment, said arrangement comprising: a patient-receiving first enclosure having a patient contacting periphery; a patient-enclosure sealing mechanism arranged with respect to the patient contacting periphery of the enclosure; and a hand manipulable patient-treating fluid discharge gun extendable through the enclosure for providing controllable treatment fluid to the wound on the patient within the enclosure; and a waste treatment fluid drainage and collection system in one-way communication from the enclosure. The fluid drainage and collection system may be gravity fed. The fluid drainage and collection system may be fed by pressure. The fluid drainage and collection system may be removable from the enclosure and replaceable with a further fluid drainage and collection system. The fluid drainage and collection system may include a disinfectant within the collection system.

The invention also includes a pulsatile lavage arrangement for the prevention of aerosol contamination so as to safely and effectively treat a wound on a patient without contaminating attending personnel and associated equipment, said arrangement comprising: a patient-receiving first enclosure having a patient contacting periphery; a hand manipulable patient-treating fluid discharge gun extendable through the enclosure for providing controllable treatment fluid to the wound on the patient within the enclosure; and a waste treatment fluid drainage and collection system in one-way discharge communication from the enclosure. The fluid discharge gun may provide a temperature, pressure and mixture controlled fluid onto a patient within the enclosure. The enclosure may be maintained at atmospheric pressure for treating a patient. The enclosure may be transparent and flexible. The enclosure may comprise a flexible bag having patient treating means therein. The patient treating means may comprise electrical components as part of the bag for effecting the healing process of the patient.

BRIEF DESCRIPTION OF THE DRAWINGS

The objects and advantages of the present invention will become more apparent when viewed in conjunction with the following drawings, in which.

DETAILED DESCRIPTION OF THE PREFERRED EMBODIMENTS

Figure 1:
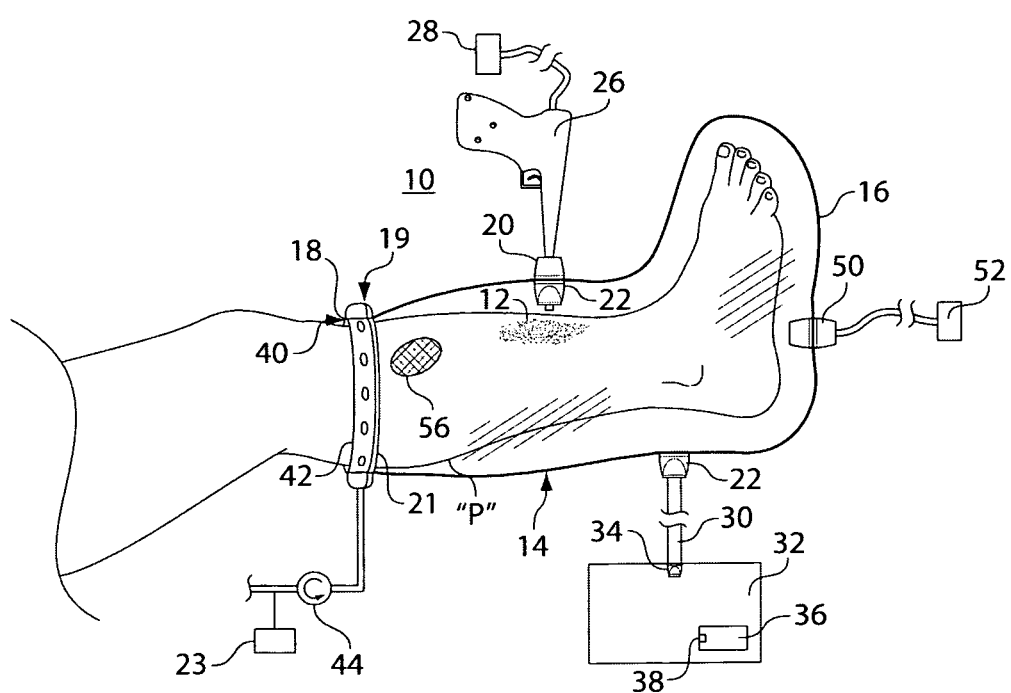
FIG. 1 is a side elevational view of a wound irrigation containment system for treating for example, a patient's limb such as a leg.

Referring now to the drawings in detail, and particularly to FIG. 1, there is shown the present invention which comprises a wound containment arrangement 10 for enclosing an entire patient, or a wound 12 on the surface of a patient "P". The wound treating arrangement 10, for example, may comprise an elongated flexible, generally tubular plastic bag 14 having a closed distal end 16 and an open proximal end 18 for keeping a patient/wound clean from both outside contamination and for preventing patient wound contamination/debris and or bacteria from spreading beyond the patient and or the patient's wound site.

The open proximal end 18, in a first embodiment thereof, has a skin engaging cuff 19 arranged therearound. The elongated enclosure bag 14 itself, has one or more entry ports 20 disposed externally thereto. Each respective entry port 20 has an internally directed duck bill valve 22 arranged thereadjacent. The entry port 20 and the duck bill valve 22 thus are in longitudinal alignment and are in fluid communication with one another. The entry port 20 and duck bill valve 22 permits a nozzle 24 of a fluid discharge gun type control mechanism 26 to extend therethrough.

A gun type control mechanism 26 permits the aiming and fluid control of a pressurized liquid and/or gas jetted through the gun 26 from a temperature, pressure and medicament controlled source 28, through the nozzle 24 and onto the wound site 12 for treatment within the enclosure bag 14. The enclosure bag 14 in one preferred embodiment has at least one duck bill drain valve 22 arranged on a lower outer portion thereof, which duck bill valve 22 is in fluid communication with a gravity and/or pressure fed drain line 30 which leads to a collection bag 32. The drain line 30 and collection bag 32 preferably have a duck bill valve 34 entry to permit the collection bag 32 to receive and contain but not leak any collection of debris from the patient "P" being treated.

A sanitizer means 36 is preferably disposed in a dissolvable pouch 38 which pouch 38 is disposed within the collection bag 32. The sanitizer means 36 is preferably dissolvable, and permits the dis-infection and decontamination of any bacteria, fluid or debris collected from the wound of the patient "P" being treated in the enclosure bag 14.

The cuff 19 at the proximal end 18 of the enclosure bag 14 in one embodiment, may have a soft, tissue sensitive, foraminous annular surface 40 with a fluid conduit 42 extending therearound. That fluid conduit 42 in the cuff 19 is in fluid communication with a pressure and/or suction pump 44 arranged downstream thereof. In use as a suction system, the pump 44 permits a vacuum to be applied to the foraminous inner annular surface 40 of the cuff 19 so as to snugly and safely secure the proximal open end 18 of the enclosure bag 14 to the skin of the patient "P", while also may be arranged to extract any extra stray contaminants or wound debris, while not irritatably rubbing against a limb or surface of the patient "P" being treated.

A further embodiment of the cuff 19 is represented in FIG. 1 wherein the cuff 19 is a positively pressurizable conduit, having a separate conduit 21 therein to function as a tourniquet. The tourniquet conduit 21 may be controlled by a processor 23 to variably control the pump 44 for squeezing a patient's limb for a determined period of time, acting as the tourniquet or a blood pressure monitor for assistance to medical personnel. Such a system included miniaturized processor 23 may also have radio frequency capabilities to alert treating medical personnel as to the location, medical needs and/or stability or instability of the patient being treated. Such a portable system for patient treating, monitoring and locating is particularly advantageous in a military setting.

In yet a further embodiment of the present invention, an air vent 50 with a pressurizable, temperature regulatable air, liquid or gaseous treatment fluid supply 52 may be arranged in fluid communication through the wall of the enclosure bag 14, as shown in FIG. 1. The air vent 50 is in communication with a pump supply 52 to provide the air, liquid or treatment gases within the enclosure bag 14 so as to space the inside surface of the enclosure bag 14 a distance apart from the skin of the patient "P" therewithin. The enclosure bag 14 may have an air pressure relief valve 56, to control and/or limit fluid pressure and permit the pressurized air provided to the enclosure bag 14 to gently escape, thus maintaining a constant or controllable pressure and/or temperature and/or medicament supply within the bag 14 and against the patient's skin.

Figure 2:
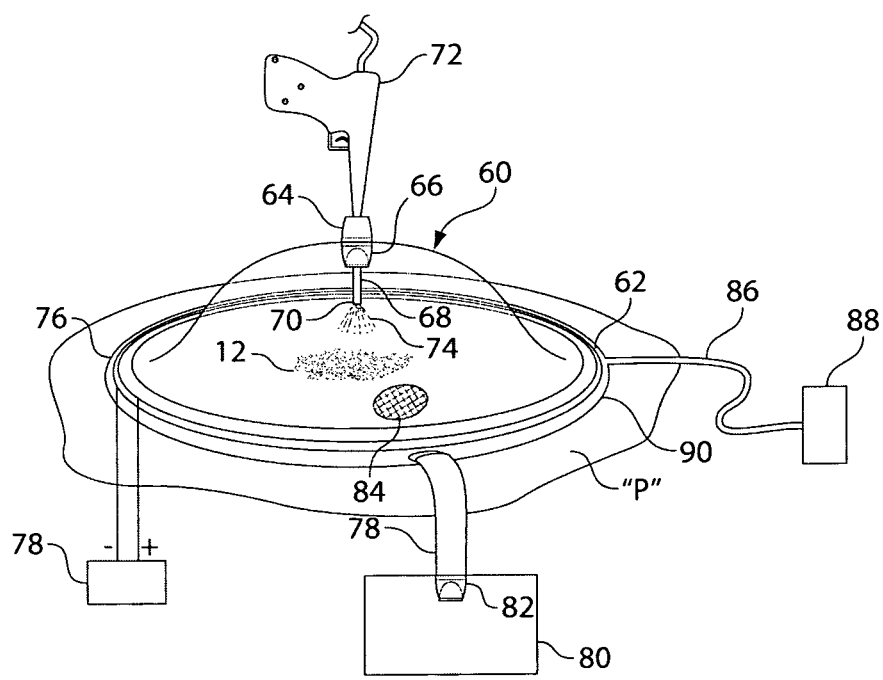
FIG. 2 is a perspective view of a wound enclosure bubble for treating of a wound on a skin surface of a patient.

A further embodiment of the present invention is contemplated by a flexible fluid pressurizable, bubble-like enclosure arrangement 60 which may be of generally hemispherical shape with an annular edge or lip 62 extending therearound for attachment to the patient's skin, as shown in FIG. 2. The bubble enclosure arrangement 60 could also be of elongated or annular shape in other embodiments, (but not shown for clarity of the figures). The bubble enclosure 60 is designed to be placed over a wound site 12 of the patient "P". Such an enclosure bubble 60 may have one or more input ports 64 on an outer or external side of the pressurized enclosure bubble 60, and a corresponding one-way duck bill valve 66 or the like arranged in longitudinal alignment with the input port(s) 64 on the outside surface of that enclosure bubble 60. The input port 64 and the duck bill valve 66 are in longitudinal alignment so as to permit the barrel 68 of a regulatable, manual hand or robot manipulable pressurizable fluid supply nozzle 70 to extend therethrough. The nozzle 70 would be the distal part of a gun-type control mechanism 72 which permits the aiming and the pressure, temperature and/or medicament fluid mixture control of a pressurized wound cleansing or medicament fluid 74 passing therethrough.

The enclosure bubble 60 (or enclosure bag of the previous figures) in this embodiment may also include an arrangement of electrical conduits or wires 76 extending around the annular lip 62 of the enclosure bubble 60, the wires 76 connected to a controllable electrical source 78 to provide a magnetic, electrical or rf stimulation treatment in an encompassing annular or rectilinear pattern around the wound 12 of the patient "P", so as to promote temperature control, radiation, heating and/or stimulate healing and normal tissue growth. A gravity or a positive or negative pressure fed drainage conduit 78 may extend under or through the side of the wall of the enclosure bubble 60 and into a collection bag 80 through a one way duck bill valve 82, similar to those as identified hereinabove. An air seepage vent 84 may be arranged adjacent the drainage conduit 78 or a spot nearby. Such seepage vent port 84 may help provide a controlled pressure and temperature atmosphere within the enclosure bubble arrangement 60 on the patient "P". A fluid supply conduit 86 may be in communication with a controllable pressure and/or suction pump 88, in which the conduit 86 is in fluid communication with a section cuff 90 disposed in the annular lip or peripheral lip 62 of the enclosure bubble 60. Such a suction pump 88 would help hold the enclosure bubble 60 to the patient "P" with minimum adverse reaction to the patient, and may also provide a secondary pressure control and/or drain for motion induced patient tissue-stimulation and/or wound treatment fluid removal. Further patient skin attachment systems may of course include adhesive or bandages of the like.

Figure 3:
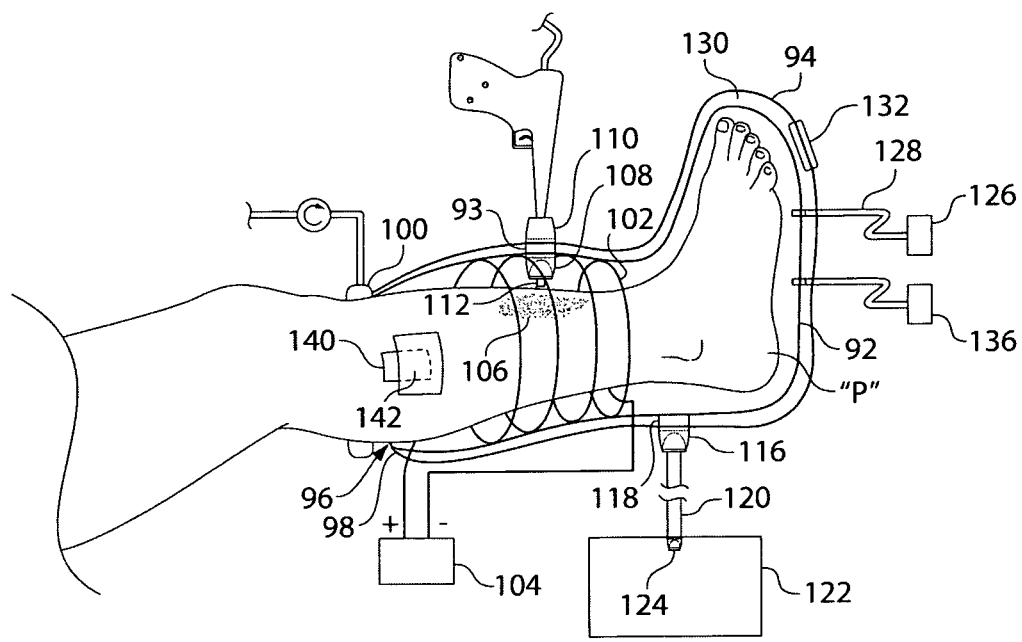
FIG. 3 is a side elevational view of a further embodiment of the elongated enclosure bag shown in FIG. 1.

In yet a further embodiment of the present invention represented in FIG. 3 comprises a first and a second enclosure bag arrangement 92 and 94 successively disposed onto or about a patient's limb. In an operative example, such an inner bag 92 and an outer bag 94 would be elongated so as to, for example fit over a patient's leg or foot having their opened ends 96 and 98 at its proximal end thereof. Such opened ends 96 and 98 would be fitted against a patient's leg and may be held thereagainst by a suction cuff 100 (or pressure cuff—for tourniquet application or patient sensing means) as in the aforementioned embodiments.

In the yet further embodiment of the present invention, it is contemplated that a spiral or a plurality of conduits (fluid pressurized or electrically conductive) wire loops 102 may be arranged peripherally about the inner side or the outer bag 94, and/or on the outer side of the inner bag 92, or disposed between the spaced apart enclosure bags 92 and 94. The loops or spiral pattern of conduits/wire 102 are in fluid and/or electrical communication with a controllable pressure/temperature and/or electrical source 104 so as to provide either cooling/heating, radio frequency (rf) treatment wherein those conduits/wires 102 could comprise a piezoelectric arrangement to induce rf wave energy for ultrasound treatment of the wound 106 therewithin, or for establishing a powered rf signal to a radio source for emission of a patient location beacon or treatment needs signal.

It is still contemplated that an inner end of an inner duck bill valve 108 on the inner bag 92 would be in fluid communication through a connector conduit 93 with an outer port 110 arranged in the outer bag 94. The nozzle 112 of a hand manipulable treatment gun 114 would extend through the outer port 110 and the inner duck bill valve 108 so as to permit controlled treatment fluid to be pressurizably disposed against the wound 106 within the inner enclosure bag 92.

A further embodiment would include a duck bill valve 116 extending from a conduit 118 which is in communication with the innermost enclosure bag 92. The duck bill valve 116 would also be in pressurized and or gravity fed fluid-drainage communication with a conduit 120 which extends to a collection bag 122. A one-way type duck bill valve 124 would be arranged within the collection bag 122 so as to prevent any backflow of contaminated fluid extending to return into the inner enclosure bag 92.

It is further represented in FIG. 3, that a pressure source 126 might direct fluid either gaseous matter or hardenable liquid through a channel 128 to the space 130 between the inner bag 92 and the outer enclosure bag 94. An air/fluid seepage patch 132 might be arranged on the outer surface of the outer bag 94 to permit controlled release and separation between the inner bag 92 and the outer bag 94.

A controllable higher pressure fluid discharge nozzle 136 may be arranged through both the outer and the inner bags 92 and 94 so as to provide the fluid pressure to the patient's tissue within the inner bag 92. Such a high pressure source would controllably separate the inner bag 92 from the patient's skin.

The fluid source 126 arranged in communication with the outer bag 94 from the pressure source through the outer bag 94 may be replaced by an settable fluid or foam injection component for splinting the patient's limb/leg which is enclosed within the inner bag 92. Such a settable, hardenable foam could press the inner bag 93 against the patient's limb and be contained within the confines of the outer bag 94 to provide a temporary or long term splint for a broken limb or the like.

It is further contemplated by the present invention, that portions 140 and/or 142 of the inner and/or the outer bag 92 and 94 may be an electrically conductive plastic and/or thermally conductive or reflective or piezo stimulative for electrical signal generation through a proper circuit and or for treating or heating tissue at the patient's wound site within the inner enclosure 92.

Figure 4:
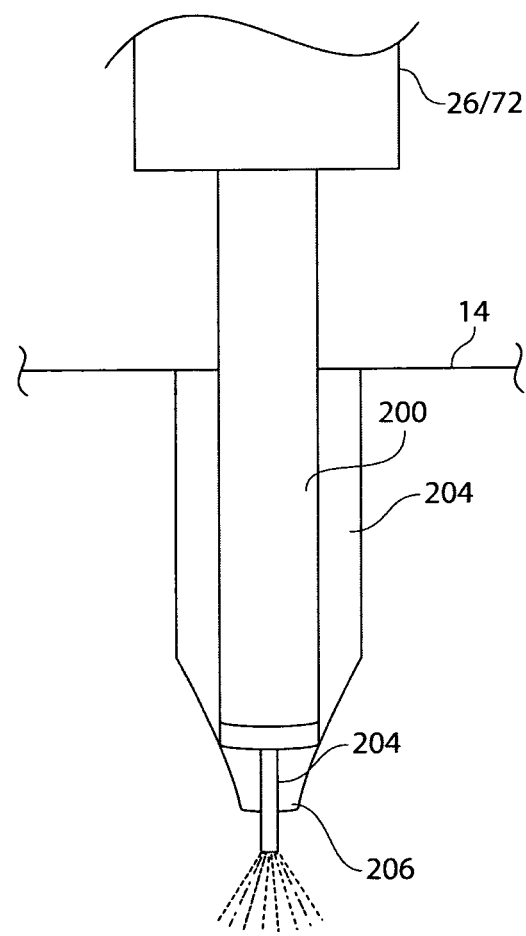
FIG. 4 is a side elevational view of an elongated inlet port or valve showing an elongated barrel and nozzle therethrough.

FIG. 4 represents an embodiment of a barrel 200 and nozzle 202 which extends from the gun-type control mechanism 26/72, shown in FIGS. 1 and 2. The barrel 200 and nozzle 202, as part of the gun type control mechanism 26/72 permits the aiming and the pressure, temperature or fluid mix control of a pressurized wound cleansing or medicament fluid(s) passing therethrough. The inlet valve 204, through which the elongated barrel 200 and nozzle 202 extend, itself may be elongated so as to sterilely enclose that elongated portion of the barrel 200, to eliminate the need for subsequent sterilization of that barrel 200 in a further use thereof. The distal tip, for example, the nozzle 202, may be of stepped or reduced diameter so as to snuggly mate through an innermost distal opening 206 of the inlet valve 204, thereby making only the nozzle 202, necessarily sterilizable or replaceable during subsequent use thereof. The nozzle tip 202 may be unscrewably removable from the barrel 200 to facilitate that replacement or cleansing.

Thus it has been shown a unique combination of treatment and containment for a wound which treatment and containment may be done by trained medical personnel and/or by emergency workers. Such containment system provides a sterile atmosphere and an arrangement for keeping the patient from becoming contaminated himself.

I claim:

1. A containment arrangement for safely and effectively treating a wound on a patient without contaminating attending personnel, comprising:
    a patient-receiving wound-treatment first enclosure bag having a patient contacting periphery;
    a pressurizable source in communication with a patient received in said wound-treatment enclosure bag through a wall of said wound-treatment enclosure bag for enlarging said enclosure bag;
    a sealing means arranged in a patient contacting periphery; and
    a hand manipulable fluid discharge barrel and nozzle extendable through said wound-treatment enclosure bag for providing controllable treatment fluid to the wound on a patient within said wound-treatment enclosure bag, wherein said nozzle extends through an inlet port and a one way valve.

2. The containment system as recited in claim 1, wherein said sealing means comprises a suction arrangement to hold said periphery of said first enclosure against a patient within said enclosure bag.

3. The containment system as recited in claim 2, wherein said sealing means also comprises a contaminated fluid removal system.

4. The containment system as recited in claim 1, wherein said patient-receiving first enclosure bag includes an electric patient-treatment-means built into the first enclosure bag.

5. The containment system as recited in claim 4, wherein said electric patient treatment means comprises an arrangement of electrically conductive members arranged around said first enclosure bag.

6. The containment system as recited in claim 5, wherein said first enclosure has a peripheral lip, and wherein said conductive members are arranged in said lip of said first enclosure bag.

7. The containment system as recited in claim 5, wherein said conductive members are arranged on a wall portion of said first enclosure bag.

8. The containment system as recited in claim 1, including a second enclosure arranged outwardly of said first enclosure bag.

9. The containment system as recited in claim 8, including a separate pressurizable system is arranged for said second enclosure.

10. The containment system as recited in claim 9, wherein said separate pressurizable system for said second enclosure includes a fluid injecting arrangement and a pressure releasing arrangement.

11. The containment system as recited in claim 9, wherein said separate pressurizable system for said second enclosure comprises a foam injection arrangement to provide a splint forming arrangement for a patient within said enclosure bag.

12. The containment system as recited in claim 1, wherein said enclosure bag includes a flexible metallic member to permit radio frequency treatment of the wound of a patient within said enclosure bag.

13. The containment system as recited in claim 9, wherein an arrangement of conduction controlled electrical conduits are arranged within said outer enclosure about a patient within said enclosure bag.

14. The containment system as recited in claim 1, wherein said enclosure bag has a contaminated fluid collection bag attached thereto, by a conduit therebetween, said collection bag containing a fluid sanitizer means therein.

15. The containment system as recited in claim 1, including a cuff sensor arranged therewith for sensing a patient's medical condition.

16. The containment system as recited in claim 15, wherein said cuff includes a tourniquet for preventing blood loss from a patient using said system.

17. The containment system as recited in claim 1, including a patient monitoring and reporting arrangement therewith for monitoring and reporting vital signs of a patient being treated therewith.

18. The containment system as recited in claim 17, wherein said monitoring and reporting arrangement includes a radio signal generation arrangement for reporting the physical location of a patient being treated.

19. The containment system as recited in claim 1, wherein said inlet port comprises a sealed arrangement around a distal end of said barrel and nozzle arrangement.

20. The containment system as recited in claim 19, wherein said nozzle is removable from said barrel.

* * * * *